United States Patent [19]
Swabby et al.

[11] Patent Number: 5,891,707
[45] Date of Patent: Apr. 6, 1999

[54] SYSTEM FOR PRODUCING *ENTEROCYTOZOON BIENEUSI* LIVE ORGANISMS

[76] Inventors: Kenna Diane Swabby; Allen R. Cahill, both of 1304 E. Bell Rd., Box 101, Phoenix, Ariz. 85022

[21] Appl. No.: 876,443

[22] Filed: Jun. 16, 1997

[51] Int. Cl.$^6$ .............................. C12N 1/00; C12N 1/02; C12N 1/04; C12N 1/10
[52] U.S. Cl. .................... 435/243; 435/260; 435/261; 435/947
[58] Field of Search ..................... 435/243, 260, 435/261, 947

[56] References Cited

U.S. PATENT DOCUMENTS 5,292,725  3/1994  Prendergast ............................... 514/46

OTHER PUBLICATIONS

Visvesvara et al. J. Eukaryotic Microbiol. vol. 42(5), pp. 506–510, Abstract enclosed, 1995.
Tzipori et al. J. Infect. Dis. vol. 175 (4), pp. 1016–1020, Abstract enclosed, 1997.

*Primary Examiner*—Leon B. Lankford, Jr.
*Assistant Examiner*—Christopher R. Tate
*Attorney, Agent, or Firm*—Martin L. Stoneman

[57] ABSTRACT

Described is a system for efficiently producing live *Enterocytozoon bieneusi* (*E. bieneusi*) organisms using laboratory animals, preferably Mongolian gerbils. Some important steps are: providing at least one breeding pair; administering to each of such breeding pair a sufficient antibiotic in sufficient dosage to destroy essentially all parasites which might be passed to offspring, especially Trichomonas; permitting such breeding pair to produce and rear offspring as production animals; preventing breeding by the production animals by separating males from females in separate cages; immune-suppressing each production animal sufficiently to permit propagation of live *E. bieneusi* organisms; infecting each production animal with love *E. bieneusi* organisms administered in an amount sufficient for such organisms to propagate but insufficient to kill the production animal; and, during a production period following such infecting, collecting the feces of each production animal. The collected fecal material is then prepared for use.

39 Claims, 4 Drawing Sheets

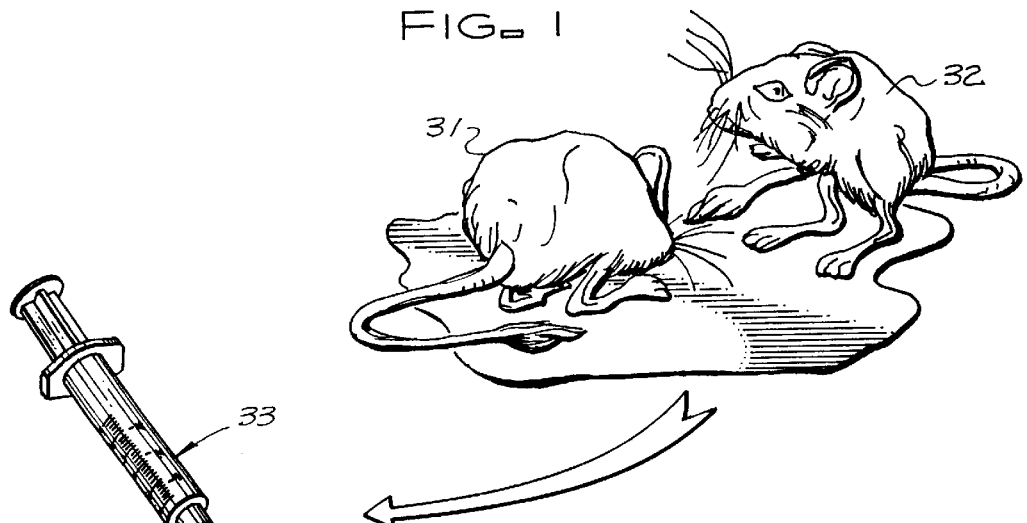
FIG. 1
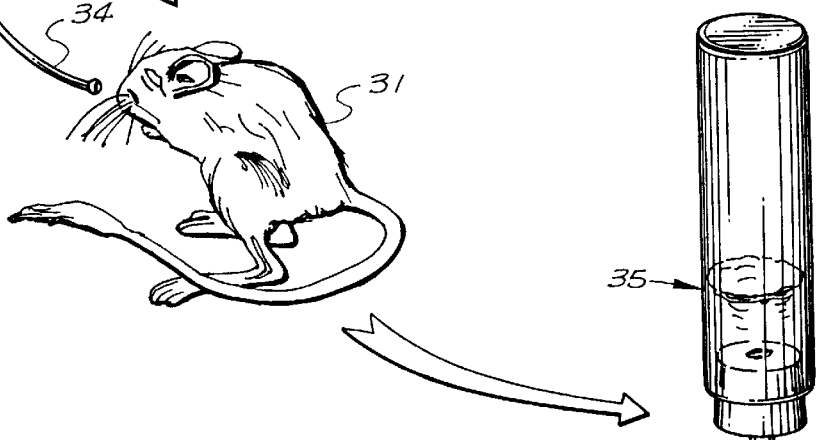
FIG. 2
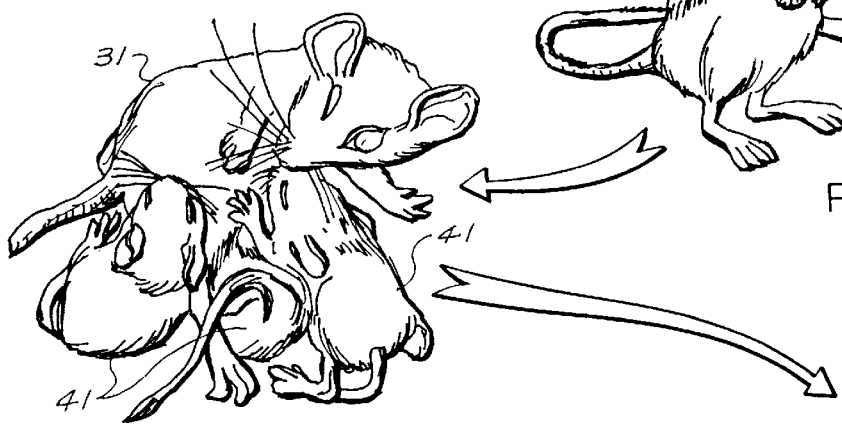
FIG. 4
FIG. 3

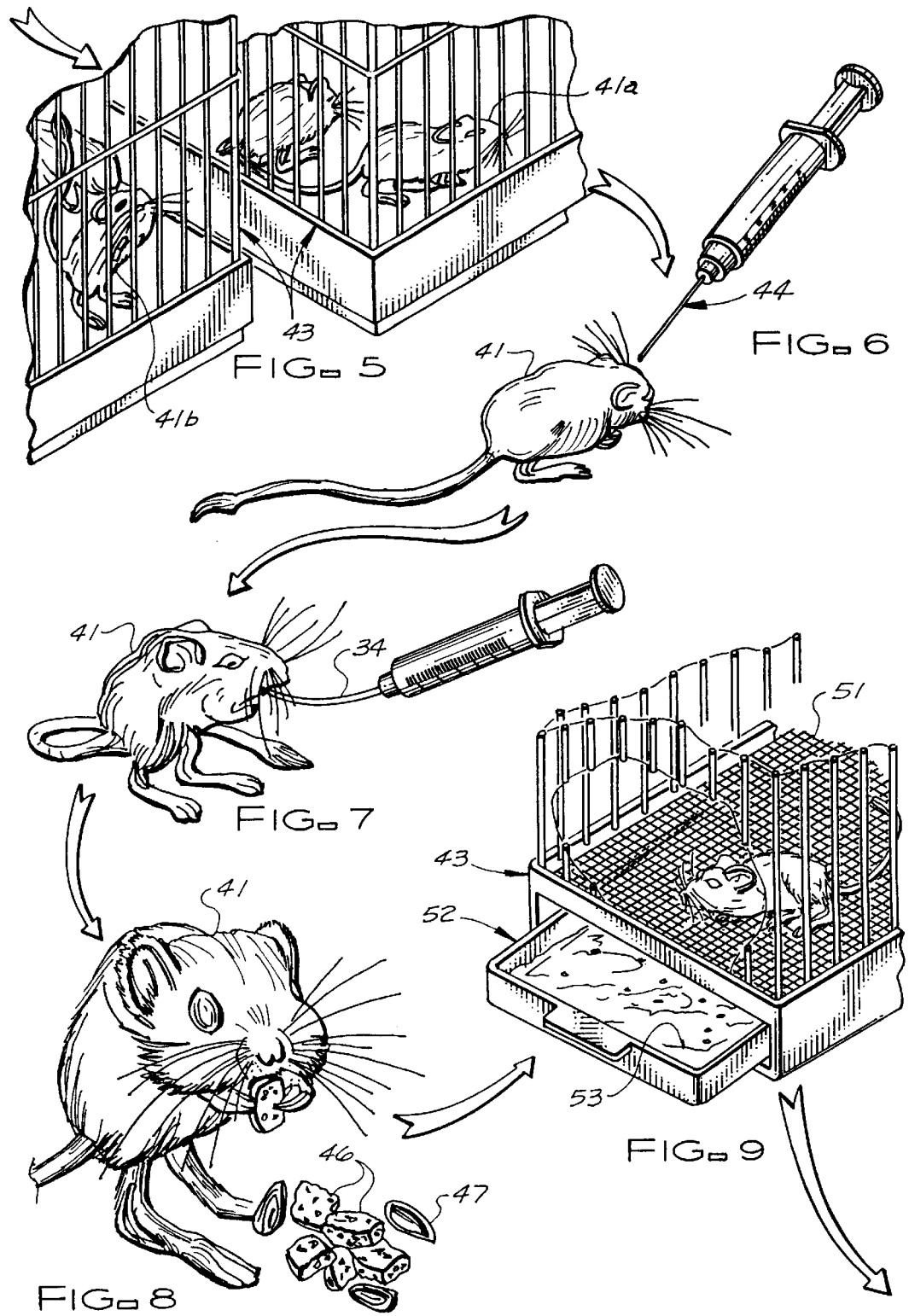

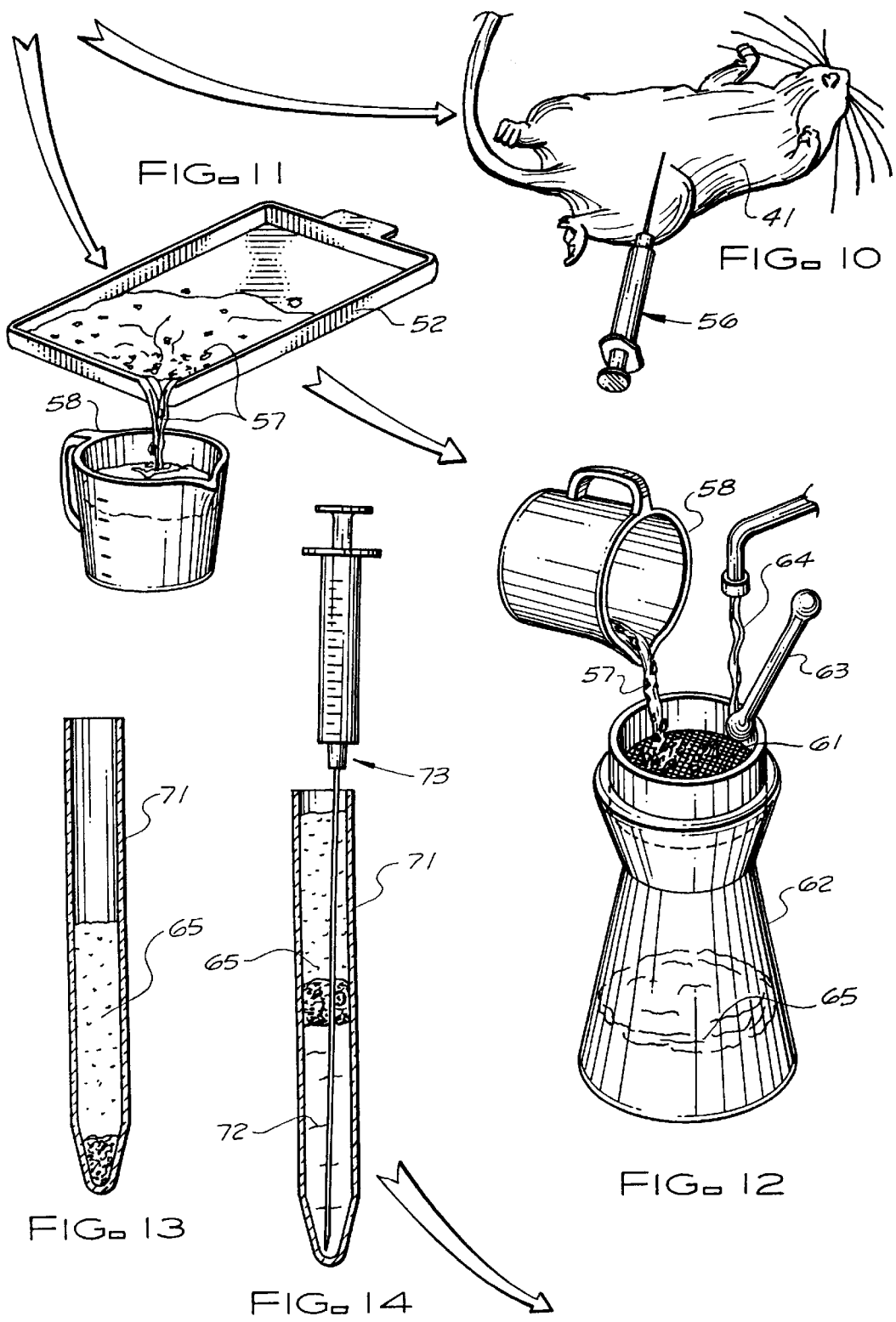

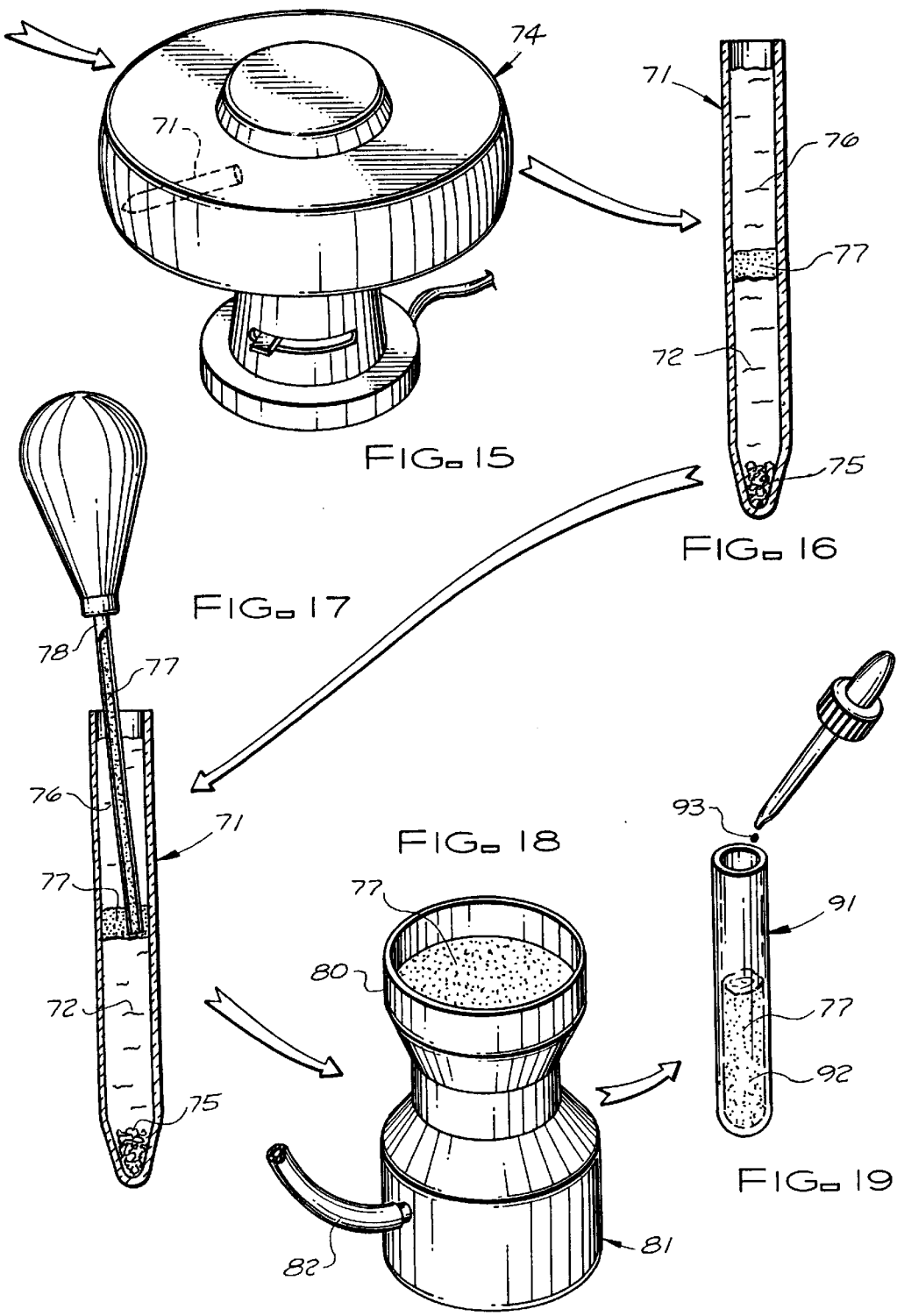

SYSTEM FOR PRODUCING *ENTEROCYTOZOON BIENEUSI* LIVE ORGANISMS

BACKGROUND OF THE INVENTION

1. Field of the Invention

This invention relates to a system for producing *Enterocytozoon bieneusi* (*E. bieneusi*) live organisms. More particularly, this invention concerns efficient production methods for *Enterocytozoon bieneusi* live organisms and the products resulting therefrom.

2. Description of the Prior Art

Typically, in the testing of possible AIDS victims, testing kits attempt to help in assessing whether the patient is infected with *E. bieneusi* live organisms, an infection of the type rarely found in persons with normal immune systems. Companies making such testing kits ideally would like to provide a large supply of IFA (Indirect Fluorescent Antibody), and/or DFA (Direct Fluorescent Antibody), and/or ELISA (Enzyme-Linked Immuno-Sorbent Assay), and/or C-ELISA (modified ELISA), as well as live *E. bieneusi* live organisms for use as controls, for use in such testing kits. But it has been found to be difficult to grow such live organisms except in AIDS patients, making the supply of such live organisms, both for direct use and for making such sera, very expensive and difficult to obtain in large quantities.

OBJECTS OF THE INVENTION

A primary object of the present invention is to fulfill the above-mentioned need by the provision of an efficient system for producing such *E. bieneusi* live organisms using other animals (and not humans). In addition, it is a primary object of this invention to provide such a system for such and other hard-to-grow organisms, in connection with its resulting novel products, in a useful form for test kit manufacturers. Other objects of this invention will become apparent with reference to the following invention descriptions.

SUMMARY OF THE INVENTION

According to a preferred embodiment of the present invention, this invention provides a system for the efficient production of *E. bieneusi* live organisms comprising the steps of: providing at least one breeding pair of mammals; administering to each of such breeding pair a sufficient antibiotic in sufficient dosage to destroy essentially all parasites which might be passed to offspring and inhibit in such offspring such efficient production of *E. bieneusi* live organisms; permitting such breeding pair to produce and rear such offspring as production animals; preventing breeding by such production animals; immune-suppressing each such production animal sufficiently to permit propagation of *E. bieneusi* live organisms; infecting each such production animal with *E. bieneusi* live organisms administered in an amount sufficient for such organisms to propagate but insufficient to kill such production animal; and during a production period following such infecting, collecting the feces of each such production animal. It also provides such a system further comprising the step of, after such collecting of such feces, screening such feces to remove any large particles to provide filtered fecal material. And it provides the product which results from practicing such a system.

Furthermore, this invention provides such a system further comprising the step of, during such production period, feeding each such production animal a diet sufficient to provide a non-sticky such feces to a level consistent with efficient such collecting of such feces; and, further comprising the step of, after such administering to each of such breeding pair such sufficient antibiotic in such sufficient dosage to destroy essentially all such parasites which might be passed to such offspring and inhibit in such offspring such efficient production of *E. bieneusi* live organisms, establishing sufficient gut flora in each of such breeding pair for adequate digestive function without interfering with such destruction of such parasites. And it provides such a system further comprising the step of, during such production period, feeding each such production animal a supplement sufficient to prevent dehydration and minimize intestinal chemical imbalances; and, further, wherein such mammals comprise gerbils. It also provides such a system wherein such collecting step comprises the step of, during such production period, maintaining each such production animal supported upon a support surface structured and arranged to permit such feces and other waste material to drop through such support surface; and, further, the step of catching such dropping feces and such dropping waste material in a container holding sufficient water for keeping such feces moist until such collection; and, further, the step of collection of all contents of such container, thereby providing a fecal material comprising such feces, such waste material, and such water. Also, it provides such a system further comprising the step of screening such fecal material to remove any large particles, thereby providing filtered fecal material containing *E. bieneusi* live organisms. And it provides the product which results from practicing such a system.

Moreover, the present invention provides such a system further comprising the step of separating *E. bieneusi* live organisms from such filtered fecal material; and, further, wherein such separating step comprises the steps of adding to such filtered fecal material a heavy liquid having a specific gravity of at least about 1.15 to provide centrifugable material, centrifuging such centrifugable material to provide a first layer of essentially *E. bieneusi* live organisms between a second layer of essentially such heavy liquid and a third layer of essentially such water, and separation of such *E. bieneusi* live organisms from such centrifugable material; and, further, wherein such separation step comprises the steps of removing essentially all the first-layer material in such first layer from such centrifugable material, and filtering such first-layer material. It further provides such a system wherein such filtering step comprises the steps of a first filtering through a small enough screen to catch any particles larger than a such *E. bieneusi* live organism, a second filtering through about an *E.-bieneusi*-size screen to remove most of such *E. bieneusi* live organisms, placing such removed *E. bieneusi* live organisms into a clean container with a small amount of purified water, a third filtering through a substantially-less-than-*E.-bieneusi* size screen to remove any remaining such *E. bieneusi* live organisms, and placing such remaining *E. bieneusi* live organisms into such clean container to provide purified *E. bieneusi* live organisms. And it provides such a system further comprising the step of adding sufficient bacteria suppressant to such purified *E. bieneusi* live organisms to suppress any bacteria; and, further comprising the step of sealing and refrigerating such clean container, for storage until use.

Additionally, in accordance with a preferred embodiment thereof, the present invention provides a system for the efficient production of *E. bieneusi* live organisms comprising the steps of: providing at least one breeding pair of Mongolian gerbils; administering to each of such breeding pair a sufficient antibiotic in sufficient dosage to destroy essentially all of Trichomonas protozoa in each of such breeding pair; permitting such breeding pair to produce and rear offspring as production animals; preventing breeding by such production animals; immune-suppressing each such production animal sufficiently to permit propagation of *E. bieneusi* live organisms; infecting each such production animal with *E. bieneusi* live organisms administered in an amount sufficient for such organisms to propagate but insufficient to kill such production animal; and, during a production period following such infecting, collecting the feces of each such production animal. Also, it provides such a system wherein such immune-suppressing step comprises injection under the skin with methylprednisolone acetate in a dosage of about 4 mg. for about a 100 gram gerbil, with the same dosage repeated about three days later, and such sufficient antibiotic in sufficient dosage comprises metrodinazole hydrochloride administered once daily for five days orally at a daily dosage of about 30 mg. per pound of animal weight, repeated after about six months.

Even further, this invention provides such a system further comprising the step of, during such production period, feeding each such production animal a diet of high-protein dog food, with an addition of a few black sunflower seeds. It also provides such a system further comprising the step of, after such administering to each of such breeding pair such sufficient antibiotic in such sufficient dosage to destroy essentially all such Trichomonas protozoa, administering gut flora and a weak antibiotic to each of such breeding pair sufficiently to establish sufficient gut flora for adequate digestive function without interfering with such destruction of such Trichomonas protozoa; and, further, wherein such step of administering gut flora and a weak antibiotic comprises placing in the drinking water of each of such breeding pair about 5 mg. of tetracycline hydrochloride per cc. of drinking water for about 5 days. Further, it provides such a system further comprising the step of, during such production period, feeding each such production animal a supplement sufficient to prevent dehydration and minimize intestinal chemical imbalances, wherein such supplement comprises a pet drink comprising fructose. And it provides such a system wherein such collecting step comprises the step of, during such production period, maintaining each such production animal supported upon a support surface structured and arranged to permit such feces and other waste material to drop through such support surface; and, further, wherein such support surface comprises open mesh material sufficient for such feces to fall through, yet providing ample support and footing for such gerbils, wherein such open mesh material comprises a ¼-inch wire cloth.

Even additionally, this invention provides such a system wherein such collecting step further comprises the step of catching such dropping feces and such dropping waste material in a container holding sufficient water for keeping such feces moist until such collection, wherein such container comprises a shallow pan suitable for holding a pond about ¼-inch deep of distilled water; and, further, wherein such collecting step further comprises the step of collection of all contents of such container, thereby providing a fecal material comprising such feces, such waste material, and such water; and, further comprising the step of screening such fecal material to remove any large particles, thereby providing filtered fecal material containing *E. bieneusi* live organisms; and, further, wherein such screening comprises, using a small amount of additional distilled water, pouring and mushing through a strainer screen, of about 250 mesh size, placed atop a beaker.

Yet further, this invention provides such a system further comprising the step of separating *E. bieneusi* live organisms from such filtered fecal material, wherein such separating step comprises the steps of: adding to such filtered and fecal material a heavy liquid having a specific gravity of at least about 1.15 to provide centrifugable material; centrifuging such centrifugable material to provide a first layer of essentially *E. bieneusi* live organisms between a second layer of essentially such heavy liquid and a third layer of essentially such water; and separation of such *E. bieneusi* live organisms from such centrifugable material; and, further, wherein such adding is done in a glass tube, after filling such glass tube about half full of such filtered fecal material such heavy liquid comprises zinc sulfate, such heavy liquid is injected into a bottom portion of such glass tube with a long needle syringe, and such centrifuging comprises placing such glass tube in such centrifuge, and spinning down such glass tube for about 15 minutes at about 2,000 RPM, whereby waste sediment from such filtered fecal material is at such bottom portion, such zinc sulfate is directly above such waste sediment and below such *E. bieneusi* live organisms, and water is above such *E. bieneusi* live organisms.

Yet additionally, it provides such a system wherein such separation step comprises the steps of removing essentially all the first-layer material in such first layer from such centrifugable material, and filtering such first-layer material; and, further wherein such filtering step comprises the steps of a first filtering through an about-3-micron membrane pre-filter above a container with a vacuum source, a second filtering through about an *E.-bieneusi*-size screen of about 1 micron to remove most of such *E. bieneusi* live organisms, placing such removed *E. bieneusi* live organisms into a clean container with a small amount of purified water, a third filtering through a less-than-*E.-bieneusi* size screen of about 0.4 micron to remove any remaining such *E. bieneusi* live organisms from such purified water, and placing such remaining *E. bieneusi* live organisms into such clean container to provide purified *E. bieneusi* live organisms. And it provides such a system further comprising the step of adding sufficient bacteria suppressant to such purified *E. bieneusi* live organisms to suppress any bacteria, wherein about 50 mg. of gentamycin sulfate is added to each 1 cc. of said *E. bieneusi* live organisms; and, further comprising the step of sealing and refrigerating such clean container, for storage until use.

BRIEF DESCRIPTION OF THE DRAWINGS

FIG. 1 is a perspective view of a first generation breeding pair of Mongolian gerbils used in the preferred embodiment of the system of the present invention for producing *E. bieneusi* live organisms.

FIG. 2 is a perspective view of a first generation adult gerbil, being treated to remove Trichomonas protozoa.

FIG. 3 is a perspective view of a first generation adult gerbil, being treated with a weak antibiotic to help establish a proper amount and balance of gut flora.

FIG. 4 is a perspective view of a first generation adult gerbil, raising second generation gerbils.

FIG. 5 is a perspective view of second generation offspring gerbils, separated, in preparation for producing *E. bieneusi* live organisms.

FIG. 6 is a perspective view of a second generation gerbil receiving an immune suppressant in preparation for producing *E. bieneusi* live organisms.

FIG. 7 is a perspective view of a second generation gerbil being infected with *E. bieneusi* live organisms.

FIG. 8 is a perspective view of a second generation gerbil feeding upon a specialized diet.

FIG. 9 is a perspective cut-away view, detailing a specialized production cage, for collecting droppings from infected second generation gerbils.

FIG. 10 is a perspective view of a gerbil being euthanized.

FIG. 11 is a perspective view of the retrieval from the production cage of the collecting water, droppings, and *E. bieneusi* live organisms.

FIG. 12 is a perspective view of the initial separation of the *E. bieneusi* live organisms from the large waste material.

FIG. 13 is a cross-section elevation view of a tube containing the screened collecting water, *E. bieneusi* live organisms, and remaining small waste material.

FIG. 14 is a cross-section elevation view of a tube containing the screened collecting water, *E. bieneusi* live organisms, remaining small waste material, and zinc sulfate.

FIG. 15 is a perspective view illustrating a centrifuge separating the *E. bieneusi* live organisms from the remaining waste material.

FIG. 16 is a cross-section elevation view of a tube containing *E. bieneusi* live organisms separated from the remaining waste material.

FIG. 17 is a cross-section elevation view of the *E. bieneusi* live organisms being removed from the tube containing the remaining waste material.

FIG. 18 is a perspective view of the final purification filtering of the *E. bieneusi* live organisms.

FIG. 19 is a perspective view of the final treatment of the *E. bieneusi* organisms.

DETAILED DESCRIPTION OF A PREFERRED EMBODIMENT AND THE BEST MODE OF PRACTICE

The method for the production of *E. bieneusi* live organisms begins with the preparatory steps of preparing from birth suitable host animals for said production. In FIG. 1 is illustrated a breeding pair of Mongolian gerbils (i.e., a female 31 and a male 32), a preferred type of gerbil, which are to be prepared for the purpose of producing suitable offspring for the production of *E. bieneusi* live organisms. The breeding pair 31 and 32 of Mongolian gerbils of FIG. 1, which are referred to as first generation, are not suitable for *E. bieneusi* production, and will be used for the sole purpose of producing and rearing second generation production gerbils. Mongolian gerbils are the preferred mammal for use in the system of the present invention; but other mammals may be used as less-preferred alternates. Such alternates may include, but are not limited to, goats, sheep, non-human primates, calves, cats, mice, etc.

Preparing the first generation of gerbils for producing suitable second generation offspring begins with treatment of each of the breeding pair 31 and 32 of the first generation to remove Trichomonas protozoa as shown in FIG. 2. Mongolian gerbils, as received from the supplier, are carriers of such protozoa. Trichomonas (a type of protozoa) acts as an inhibitor which interferes with the growing of the *E. bieneusi* live organisms. After the first generation of gerbils have had the Trichomonas successfully destroyed, their offspring, the second generation, will be free of this protozoa, and will not require like treatment. Thus, according to this invention, the step is provided of administering to each of the breeding pair a sufficient antibiotic in sufficient dosage to destroy essentially all of Trichomonas protozoa in each of the breeding pair, wherein a preferred such sufficient antibiotic in such sufficient dosage is metrodinazole hydrochloride (a product example is "Flagyl", a trademark of Searle Pharmaceutical, which now manufactures and sells such product) administered once daily for five days orally at a daily dosage of about 30 mg. per pound of animal weight, repeated after about six months. FIG. 2 illustrates one of the breeding pair 31 and 32 (the female 31 is illustrated, but the male, as described, gets the same treatment) about to be administered such antibiotic orally by means of measuring syringe 33, including feeding or dispensing tube 34. Such metrodinazole hydrochloride is not 100% effective, and unfortunately, Trichomonas will often regrow, and so it is preferred to repeat such dosage again six months later.

An unfortunate side effect of the metrodinazole hydrochloride treatment is the destruction of gut flora in the breeding pair, the digestive bacteria for proper digestive functioning. The types of gut flora will also be out of balance in that more of the anaerobic flora will be destroyed than the aerobic flora. Therefore gut flora must be re-established, and in proper balance, to allow proper digestive functioning. Thus, in the method of this invention, the step is provided of administering gut flora and a weak antibiotic to each of the breeding pair sufficiently to establish sufficient gut flora for adequate digestive function without interfering with the destruction of such Trichomonas protozoa. It is preferred that this step embody the giving to each of the breeding pair 31 and 32, in their drinking water, tetracycline hydrochloride (a product example is "Panmycin", a trademark of Upjohn Pharmaceutical, which now manufactures and sells such product) administered in a dosage of about 5 mg. per cc. of drinking water for 5 days. It is preferred that this step also embody the giving to each of the breeding pair 31 and 32, in such drinking water, a small amount of fecal material from healthy such gerbils, thus promoting the growth of proper gut flora, especially providing some replacement anaerobic flora for faster flora balancing. As illustrated in FIG. 3, such tetracycline hydrochloride (and such fecal material) is administered to such an example gerbil 31 by way of its drinking water dispenser 35. Such tetracycline hydrochloride administration begins immediately after such metrodinazole hydrochloride treatment, or concurrently if desired. As with the "Flagyl" (trademark) treatment, "Panmycin" (a trademark) need not be administered to the second generation.

After the first generation breeding pair 31 and 32 have been prepared as previously described, they are allowed to produce and rear their offspring 41 as suggested by the illustration of FIG. 4. These offspring 41 are referred to herein as second generation or as production animals 41, suitable for *E. bieneusi* live organism production. Thus, the present invention provides the step of permitting such breeding pair to produce and rear second generation offspring as production animals. Many times the first generation female gerbil 31 is received from the supplier already pregnant. If the delivery of her offspring takes place at least two days after the mother has been on her "Flagyl" (a trademark) treatment, the offspring may be used as second generation *E. bieneusi* producers, i.e., as production animals 41. Earlier births may contain Trichomonas and would render the young not suitable as second generation *E. bieneusi* producers. In this event, they could still be considered and used as first generation gerbils requiring the above described treatments.

Once the second generation gerbils, (the immediate offspring of the treated first generation gerbils), the production animals 41, reach an age of from approximately 30 to 60 days, they may be used to produce the desired *E. bieneusi* live organisms. Being free of the Trichomonas protozoa, they are suitable for introduction of the infecting *E. bieneusi* live organisms. In preparation for infection and growth of *E. bieneusi*, they are separated by sex (females 41a from males 41b) to prevent breeding, and placed into appropriate cages as 43 illustrated by FIG. 5. Thus, this invention provides a step of preventing breeding by the production animals by separately caging each sex before breeding capability occurs. Specific preferred cage construction features are later illustrated and described with reference to FIG. 9.

Prior to being infected with *E. bieneusi* live organisms, the production animals 41 are immune-suppressed. A weakened immune system will allow the *E. bieneusi* live organisms to easily propagate. Thus, this invention provides a step of immune-suppressing each such production animal, preferably by injection under the skin with methylprednisolone acetate (a product example is "Depo-Medrol", a trademark of Upjohn Pharmaceutical, which now manufactures and sells such product). Preferred dosage is 4 mg. (for a 90–100 gram gerbil, typical). This dosage is preferably repeated again three days later. FIG. 6 illustrates a production animal 41 being immune-suppressed by injection under the skin using hypodermic needle 44.

Once the immune system of the production animals 41 is weakened, they are infected with *E. bieneusi* live organisms by inoculating them orally with a feeding tube 34 as shown in FIG. 7. Infection is conducted as early as the same day as the second administration of the immune suppressant as described with reference to FIG. 6. Thus, this invention provides the step of immune-suppressing each production animal sufficiently to permit propagation of *E. bieneusi* live organisms, preferably by an inoculation dosage of about 10,000 live organisms per 50 grams of animal weight. The initial *E. bieneusi* live organisms may be obtained from an AIDS patient (a donor), and subsequently purified; and thereafter from production animals as herein described. The dosage size required to promote the desired infection rate is based on the goal of obtaining a good practical standard production time. If the dosage is too low, the infection will not propagate, or the onset time will be slow and the disease weak. This will also occur if the immune system has not been suitably weakened. The larger the dosage, the faster and more intense the disease will be. If the dosage is too high, it will overtake the gerbil's immune system and kill the gerbil. The specified dosage rate is as high as is practical to get a repeatable term so they will propagate themselves. Production typically continues for approximately 3 weeks after infection.

While the production animal 41 is growing and producing *E. bieneusi* live organisms, such live organisms are collected and harvested from the production animal's feces as described in FIGS. 9, 11, and following. As will be further described, and will become more apparent, the physical condition of the production animal's stool is most important. Therefore the production animal 41 is placed on a diet to provide an optimum consistency stool. Thus, this invention provides a step of, during such production period, feeding each such production animal 41 a diet of high-protein dog food 46, with an addition of a few black sunflower seeds 47 (as a promoter of gastro-colonic reflex and thus ingestion and production), as illustrated in FIG. 8. This results in feces which are not sticky and from which the *E. bieneusi* live organisms can be suitably separated. In contrast, a normal diet, which may consist of corn, barley, oats, or normal pellet feed, results in droppings which are sticky and difficult to process. In addition, this invention provides the step of, during such production period, feeding each such production animal a supplement sufficient to prevent dehydration and minimize intestinal chemical imbalances, preferably by adding to the diet of high-protein dog food a water supplement a pet drink which contains fructose and other known ingredients given to counteract intestinal upsets and acid base imbalances and to prevent dehydration, such water supplement being given much as shown in FIG. 3. An example such pet drink is that called "Thirsty Dog" (a trademark).

The cages 43 in which the production animals 41 are placed, in reference to FIG. 5, are of specialized design and construction, with features necessitated by the production task at hand and illustrated in FIG. 9. The floor surface 51 is of open mesh material, with openings sufficient for the feces to fall through, yet providing ample support and footing for the production animals 41. For Mongolian gerbils, ¼" wire cloth fulfills this requirement. Below this open mesh floor 51 is positioned a removable shallow tray or pan 52, suitable for containing a shallow (preferably abut ¼") pond 53 of distilled water, and positioned to catch all droppings which fall through the mesh floor 51. With this cage configuration, the *E. bieneusi* live organisms, produced, as by the infected production gerbils, and eliminated by such gerbils through their feces, are collected within the pan, and kept moist within the pond of distilled water. They may then be easily collected by the lab technician. Thus, this invention provides steps of, during such production period, maintaining each such production animal supported upon a support surface structured and arranged to permit such feces and other waste material to drop through such support surface, wherein such support surface comprises open mesh material sufficient for such feces to fall through, yet providing ample support and footing for such gerbils, wherein such open mesh material comprises a ¼-inch wire cloth; wherein such collecting step further comprises the step of catching such dropping feces and such dropping waste material in a container holding sufficient water for keeping such feces moist until such collection, wherein such container comprises a shallow pan suitable for holding a pond about ¼-inch deep of distilled water.

A suitable production rate of *E. bieneusi* live organisms by the production animals continues for approximately 3 weeks then typically begins tapering off. At this point production may be restarted again by re-introducing the *E. bieneusi* live organisms as previously described in FIG. 7. After this re-infecting, production of the *E. bieneusi* live organisms typically resumes in about 2 days. This method of restarting production by re-infection may be accomplished numerous times until the production animal is overtaken by an overgrowth of amoeba leaving no opportunity for further production. This point may occur after up to several months of successful production. Therefore when the production lowers to an unsuitable rate and restarting fails, the production animal 41 is to be destroyed (see FIG. 10) in a humane and safe manner. Destroying the production animal is accomplished by being put to sleep with an injectable 56 and then cremation. The reason for this safety precaution is that the production animal remains a carrier of the *E. bieneusi* live organism, and, if turned loose or escaping, could infect or contaminate in an undesirable manner.

As shown in FIG. 11, collection of the *E. bieneusi* live organisms from the cage 43 is accomplished by simply removing the tray 52 from the bottom of the cage 43 and emptying all its contents 57 by pouring into a suitable container 58. The material 57 then collected includes water, feces and other waste and the *E. bieneusi* live organisms which are mainly held in suspension in the water. Thus, this invention provides the step of collection of all contents of such pan container, thereby providing a fecal material 57 comprising such feces, such waste material, and such water.

The collected fecal material 57 is then poured through a strainer 61, preferably of a 250 mesh size, which is placed atop a convenient container such as a beaker 62, as shown in FIG. 12. The majority of the *E. bieneusi* live organisms are held in suspension in the water passing through strainer 61, with some in the sediment at the bottom of the container, and some remaining in the feces caught by the strainer 61. To capture the *E. bieneusi* live organisms in the feces retained in the strainer 61, the feces are mushed through the strainer 61 with a suitable tool 63 while utilizing a small amount of additional distilled water 64 to aide in washing them through. Thus, this invention provides a step of screening such fecal material 57 to remove any large particles, thereby providing filtered fecal material 65 containing *E. bieneusi* live organisms, wherein such screening comprises, using a small amount of additional distilled water, pouring and mushing through a strainer screen, of about 250 mesh size, placed atop a beaker. After the large waste material has been removed by the screening process, the strained solution 65 is further cleaned and purified and refined as described in FIGS. 13 through 18.

FIG. 13 illustrates a glass tube 71 filled approximately half full with the strained solution, the filtered fecal material 65, a first step in what follows. Next, as illustrated in FIG. 14, zinc sulfate (ZnSO4) 72 is injected into the bottom of the glass tube 71 and under the filtered fecal material 65, with a long needle syringe 73. As the zinc sulfate 72 has a specific gravity of 1.18, it will float the filtered fecal material 65, with its *E. bieneusi* live organisms and the remaining waste sediment. This step embodies the step in the present invention of adding to such filtered fecal material a heavy liquid having a specific gravity of at least about 1.15 to provide centrifugable material.

As illustrated in FIG. 15, next, the glass tube 71, with its filtered fecal material 65 and its zinc sulfate 72, is placed into a centrifuge 74, and spun down for approximately 15 minutes at 2,000 RPM. After such spinning, the contents of the glass tube 71 will have been separated as illustrated in FIG. 16. The zinc sulfate 72 remains at the bottom of the glass tube 71 and the waste sediment 75 part of filtered fecal material 65 that previously was floated above the zinc sulfate 72 is now at the bottom of the tube 71. The water 76 part of the filtered fecal material 65 remains at the top of the tube above the zinc sulfate. The *E. bieneusi* live organisms 77, with a specific gravity of 1.1 to 1.15, have now been separated into an interface area between the water (1.0 specific gravity) and the zinc sulfate with its specific gravity of 1.18, as shown. This step embodies in this invention the step of centrifuging such centrifugable material to provide a first layer of essentially *E. bieneusi* live organisms between a second layer of essentially such heavy liquid and a third layer of essentially such water.

Next, the *E. bieneusi* live organisms 77, in suspension in the interface area between the water 76 and the zinc sulfate 72, are drawn out with a pipette 78, as shown in FIG. 17, embodying the step in this invention of removing essentially all the first-layer material in such first layer from such centrifugable material. Next, the *E. bieneusi* live organisms 77 are placed upon a 3 micron membrane pre-filter 80, above a container 81 which is connected to a vacuum source 82, as shown in FIG. 18.

When using the vacuum source 82 to evacuate the container 81, the *E. bieneusi* live organisms 77 in suspension, being approximately 0.75–1.75 micron in size, are pulled into the container 81, and any associated waste material larger than 3 micron remains on the pre-filter 80. This step embodies in this invention the step of a first filtering through a small enough screen to catch any particles larger than a such *E. bieneusi* live organism. Next, the *E. bieneusi* live organisms 77 in suspension are removed from the container and in like manner (as FIG. 18) are placed upon a 1 micron membrane filter (otherwise, like filter 80). Upon evacuation of the new container, the majority of the *E. bieneusi* live organisms 77 are caught on the 1-micron filter, with the suspension water being drawn into the container. The separated *E. bieneusi* live organisms 77 are then removed from the membrane filter, placed into a glass tube 91 and a small amount of distilled water 92 is added. The *E. bieneusi* organism 77, not being rigid, but having a flexible shape will pass through an opening smaller than its size. Therefore, the suspension water with some remaining *E. bieneusi* live organisms, is filtered again (as in FIG. 18) with a 0.4 micron membrane filter (otherwise, like filter 80), catching the remaining live organisms 77. These then are added to the glass tube 91. These steps embody herein the steps of: a second filtering through about an *E.-bieneusi*-size screen to remove most of such *E. bieneusi* live organisms; placing such removed *E. bieneusi* live organisms into a clean container with a small amount of purified water; a third filtering through a substantially-less-than-*E.-bieneusi* size screen to remove any remaining such *E. bieneusi* live organisms; and placing such remaining *E. bieneusi* live organisms into such clean container to provide purified *E. bieneusi* live organisms. Lastly, as shown in FIG. 19, about 50 mg. of gentamycin sulfate (per each cc. of such purified *E. bieneusi* live organisms 77), in solution (as in the product "Gentocin", a trademark), is added to the glass tube 91 as by drop 93. This addition is to suppress bacteria that may inadvertently pass through the 1 micron filter. The glass tube 91 is then sealed and refrigerated until use. These steps embody in this invention the steps of: adding sufficient bacteria suppressant to such purified *E. bieneusi* live organisms to suppress any bacteria; and sealing and refrigerating such clean container, for storage until use.

Although applicant has described applicant's preferred embodiments of this invention, it will be understood that the broadest scope of this invention includes such modifications as diverse shapes and sizes and materials. Such scope is limited only by the below claims as read in connection with the above specification.

Further, many other advantages of applicant's invention will be apparent to those skilled in the art from the above descriptions and the below claims.

What is claimed is:

1. A system for the efficient production of live *Enterocytozoon bieneusi* (*E. bieneusi*) organisms comprising the steps of:

a. providing at least one breeding pair of mammals;

b. administering to each of said breeding pair a sufficient antibiotic in sufficient dosage to destroy essentially all parasites which might be passed to offspring and inhibit in said offspring said efficient production of *E. bieneusi* organisms;

c. permitting said breeding pair to produce and rear said offspring as production animals;

d. preventing breeding by said production animals;

e. immune-suppressing each said production animal sufficiently to permit propagation of *E. bieneusi* organisms;

f. infecting each said production animal with *E. bieneusi* organisms administered in an amount sufficient for said organisms to propagate but insufficient to kill said production animal; and g. during a production period following said infecting, collecting the feces of each said production animal, said feces containing the live *E. bieneusi* organisms.

2. A system according to claim 1 further comprising the step of:

a. after said collecting of said feces, screening said feces to remove any large particles to provide filtered fecal material.

3. The product which results from practicing a system according to claim 2.

4. A system according to claim 1 further comprising the step of:

a. during said production period, feeding each said production animal a diet sufficient to provide a non-sticky said feces to a level consistent with efficient said collecting of said feces.

5. A system according to claim 1 further comprising the step of:

a. after said administering to each of said breeding pair said sufficient antibiotic in said sufficient dosage to destroy essentially all said parasites which might be passed to said offspring and inhibit in said offspring said efficient production of live *E. bieneusi* organisms, establishing sufficient gut flora in each of said breeding pair for adequate digestive function without interfering with said destruction of said parasites.

6. A system according to claim 1 further comprising the step of:

a. during said production period, feeding each said production animal a supplement sufficient to prevent dehydration and minimize intestinal chemical imbalances.

7. A system according to claim 1 wherein said mammals comprise gerbils.

8. A system according to claim 7 wherein said collecting step comprises the step of:

a. during said production period, maintaining each said production animal supported upon a support surface structured and arranged to permit said feces and other waste material to drop through said support surface.

9. A system according to claim 8 wherein said collecting step further comprises the step of:

a. catching said dropping feces and said dropping waste material in a container holding sufficient water for keeping said feces moist until said collection.

10. A system according to claim 9 wherein said collecting step further comprises the step of:

a. collection of all contents of said container, thereby providing a fecal material comprising said feces, said waste material, and said water.

11. A system according to claim 10 further comprising the step of:

a. screening said fecal material to remove any large particles, thereby providing filtered fecal material containing live *E. bieneusi* organisms.

12. The product which results from practicing a system according to claim 11.

13. A system according to claim 11 further comprising the step of:

a. separating live *E. bieneusi* organisms from said filtered fecal material.

14. A system according to claim 13 wherein said separating step comprises the steps of:

a. adding to said filtered fecal material a heavy liquid having a specific gravity of at least about 1.15 to provide centrifugable material;

b. centrifuging said centrifugable material to provide a first layer essentially containing live *E. bieneusi* organisms between a second layer of essentially said heavy liquid and a third layer of essentially said water; and c. separation of said live *E. bieneusi* organisms from said centrifugable material.

15. A system according to claim 14 wherein said separation step comprises the steps of:

a. removing essentially all the first-layer material in said first layer from said centrifugable material; and b. filtering said first-layer material.

16. A system according to claim 15 wherein said filtering step comprises the steps of:

a. a first filtering through a small enough screen to catch any particles larger than a said live *E. bieneusi* organism;

b. a second filtering through about an *E.-bieneusi*-size screen to remove most of said live *E. bieneusi* organisms;

c. placing said removed live *E. bieneusi* organisms into a clean container with a small amount of purified water;

d. a third filtering through a substantially-less-than-*E. bieneusi* size screen to remove any remaining said *E. bieneusi* live organisms; and e. placing said remaining live *E. bieneusi* organisms into said clean container to provide purified live *E. bieneusi* organisms.

17. A system according to claim 16 further comprising the step of:

a. adding sufficient bacteria suppressant to said purified live *E. bieneusi* organisms to suppress any bacteria.

18. A system according to claim 17 further comprising the step of:

a. sealing and refrigerating said clean container, for storage until use.

19. A system for the efficient production of *E. bieneusi* organisms comprising the steps of:

a. providing at least one breeding pair of Mongolian gerbils;

b. administering to each of said breeding pair a sufficient antibiotic in sufficient dosage to destroy essentially all of Trichomonas protozoa in each of said breeding pair;

c. permitting said breeding pair to produce and rear offspring as production animals;

d. preventing breeding by said production animals;

e. immune-suppressing each said production animal sufficiently to permit propagation of live *E. bieneusi* organisms;

f. infecting each said production animal with live *E. bieneusi* organisms administered in an amount sufficient for said organisms to propagate but insufficient to kill said production animal; and g. during a production period following said infecting, collecting the feces of each said production animal, said feces containing the live *E. bieneusi* organism.

20. A system according to claim 19 wherein:

a. said immune-suppressing step comprises injection under the skin with methylprednisolone acetate in a dosage of about 4 mg. for about a 100 gram gerbil, with the same dosage repeated about three days later; and b. said sufficient antibiotic in sufficient dosage comprises metronidazole hydrochloride administered once daily for five days orally at a daily dosage of about 30 mg. per pound of animal weight, repeated after about six months.

21. A system according to claim 19 further comprising the step of:
   a. during said production period, feeding each said production animal a diet of high-protein dog food, with an addition of a few black sunflower seeds.

22. A system according to claim 19 further comprising the step of:
   a. after said administering to each of said breeding pair said sufficient antibiotic in said sufficient dosage to destroy essentially all said Trichomonas protozoa, administering gut flora and a weak antibiotic to each of said breeding pair sufficiently to establish sufficient gut flora for adequate digestive function without interfering with said destruction of said Trichomonas protozoa.

23. A system according to claim 22 wherein said step of administering gut flora and a weak antibiotic comprises placing in the drinking water of each of said breeding pair about 5 mg. of tetracycline hydrochloride per each cc. of drinking water for about 5 days.

24. A system according to claim 19 further comprising the step of:
   a. during said production period, feeding each said production animal a supplement sufficient to prevent dehydration and minimize intestinal chemical imbalances;
   b. wherein said supplement comprises a pet drink comprising fructose.

25. A system according to claim 19 wherein said collecting step comprises the step of:
   a. during said production period, maintaining each said production animal supported upon a support surface structured and arranged to permit said feces and other waste material to drop through said support surface.

26. A system according to claim 25 wherein said support surface comprises:
   a. open mesh material sufficient for said feces to fall through, yet providing ample support and footing for said gerbils;
   b. wherein said open mesh material comprises a ¼-inch wire cloth.

27. A system according to claim 25 wherein said collecting step further comprises the step of:
   a. catching said dropping feces and said dropping waste material in a container holding sufficient water for keeping said feces moist until said collection;
   b. wherein said container comprises a shallow pan suitable for holding a pond about ¼-inch deep of distilled water.

28. A system according to claim 27 wherein said collecting step further comprises the step of:
   a. collection of all contents of said container, thereby providing a fecal material comprising said feces, said waste material, and said water.

29. A system according to claim 28 further comprising the step of:
   a. screening said fecal material to remove any large particles, thereby providing filtered fecal material containing live *E. bieneusi* organisms.

30. A system according to claim 29 wherein said screening comprises, using a small amount of additional distilled water, pouring and mushing through a strainer screen, of about 250 mesh size, placed atop a beaker.

31. A system according to claim 29 further comprising the step of:
   a. separating live *E. bieneusi* organisms from said filtered fecal material;
   b. wherein said separating step comprises the steps of
      i. adding to said filtered fecal material a heavy liquid having a specific gravity of at least about 1.15 to provide centrifugable material;
      ii. centrifuging said centrifugable material to provide a first layer essentially containing live *E. bieneusi* organisms between a second layer of essentially said heavy liquid and a third layer of essentially said water; and
      iii. separation of said live *E. bieneusi* organisms from said centrifugable material.

32. A system according to claim 31 wherein:
   a. said adding is done in a glass tube, after filling said glass tube about half full of said filtered fecal material;
   b. said heavy liquid comprises zinc sulfate;
   c. said heavy liquid is injected into a bottom portion of said glass tube with a long needle syringe; and
   d. said centrifuging comprises
      i. placing said glass tube in said centrifuge; and
      ii. spinning down said glass tube for about 15 minutes at about 2,000 RPM;
      iii. whereby waste sediment from said filtered fecal material is at said bottom portion, said zinc sulfate is directly above said waste sediment and below said live *E. bieneusi* organisms, and water is above said live *E. bieneusi* organisms.

33. A system according to claim 31 wherein said separation step comprises the steps of:
   a. removing essentially all the first-layer material in said first layer from said centrifugable material; and
   b. filtering said first-layer material.

34. A system according to claim 33 wherein said filtering step comprises the steps of:
   a. a first filtering through an about-3-micron membrane pre-filter above a container with a vacuum source;
   b. a second filtering through about an *E.-bieneusi*-size screen of about 1 micron to remove most of said live *E. bieneusi* organisms;
   c. placing said removed live *E. bieneusi* organisms into a clean container with a small amount of purified water;
   d. a third filtering through a less-than-*E.-bieneusi* size screen of about 0.4 micron to remove any remaining said live *E. bieneusi* organisms from said purified water; and
   e. placing said remaining live *E. bieneusi* organisms into said clean container to provide purified live *E. bieneusi* organisms.

35. A system according to claim 34 further comprising the step of:
   a. adding sufficient bacteria suppressant to said purified live *E. bieneusi organisms to suppress any bacteria;*
   b. wherein about 50 mg. of gentamycin sulfate is added to each 1 cc. of said live *E. bieneusi* organisms.

36. A system according to claim 35 further comprising the step of:
   a. sealing and refrigerating said clean container, for storage until use.

37. A system for the efficient production of live *E. bieneusi* organisms comprising the steps of:
   a. providing at least one breeding pair of Mongolian gerbils;

b. administering to each of said breeding pair a sufficient antibiotic in sufficient dosage to destroy essentially all of Trichomonas protozoa in each of said breeding pair,
  i. wherein said sufficient antibiotic in sufficient dosage comprises metrodinazole hydrochloride administered once daily for five days orally at a daily dosage of about 30 mg. per pound of animal weight, repeated after about six months;
c. permitting said breeding pair to produce and rear offspring as production animals;
d. preventing breeding by said production animals by separately caging each sex before breeding capability occurs;
e. immune-suppressing each said production animal sufficiently to permit propagation of live *E. bieneusi* organisms
  i. wherein said immune-suppressing step comprises injection under the skin with methylprednisolone acetate in a dosage of about 4 mg. for about a 100 gram gerbil, with the same dosage repeated about three days later;
f. infecting each said production animal with live *E. bieneusi* organisms administered in an amount sufficient for said organisms to propagate but insufficient to kill said production animal
  i. wherein said amount comprises about 10,000 live organisms per 50 grams of animal weight administered about the same time as said second injection of said immune-suppressing step;
g. during a production period following said infecting, collecting the feces of each said production animal, said feces containing the live *E. bieneusi* organisms.

38. A system according to claim 37 further comprising the steps of:
a. after said administering to each of said breeding pair said sufficient antibiotic in said sufficient dosage to destroy essentially all said Trichomonas protozoa, administering gut flora and a weak antibiotic to each of said breeding pair sufficiently to establish sufficient gut flora for adequate digestive function without interfering with said destruction of said Trichomonas protozoa
  i. wherein said step of administering gut flora and a weak antibiotic comprises placing in the drinking water of each of said breeding pair about 5 mg. of tetracycline hydrochloride per cc. of drinking water for about 5 days;
b. during said production period, feeding each said production animal a diet of high-protein dog food, with an addition of a few black sunflower seeds;
c. during said production period, feeding each said production animal a supplement sufficient to prevent dehydration and minimize intestinal chemical imbalances;
d. wherein said collecting step comprises the step of
  i. during said production period, maintaining each said production animal supported upon a support surface structured and arranged to permit said feces and other waste material to drop through said support surface,
  ii. wherein said support surface comprises open mesh material sufficient for said feces to fall through, yet providing ample support and footing for said gerbils,
  iii. wherein said open mesh material comprises a ¼-inch wire cloth;
e. wherein said collecting step further comprises the step of
  i. catching said dropping feces and said dropping waste material in a container holding sufficient water for keeping said feces moist until said collection,
  ii. wherein said container comprises a shallow pan suitable for holding a pond about ¼-inch deep of distilled water;
f. wherein said collecting step further comprises the step of collection of all contents of said container, thereby providing a fecal material comprising said feces, said waste material, and said water;
g. screening said fecal material to remove any large particles, thereby providing filtered fecal material containing live *E. bieneusi* organisms,
  i. wherein said screening comprises, using a small amount of additional distilled water, pouring and mushing through a strainer screen, of about 250 mesh size, placed atop a beaker.

39. A system according to claim 38 further comprising the steps of:
a. separating live *E. bieneusi* organisms from said filtered fecal material;
b. wherein said separating step comprises the steps of
  i. adding to said filtered and fecal material a heavy liquid having a specific gravity of at least about 1.15 to provide centrifugable material,
  ii. centrifuging said centrifugable material to provide a first layer essentially containing live *E. bieneusi* organisms between a second layer of essentially said heavy liquid and a third layer of essentially said water, and
  iii. separation of said live *E. bieneusi* organisms from said centrifugable material
  iv. wherein
    (1) said adding is done in a glass tube, after filling said glass tube about half full of said filtered fecal material,
    (2) said heavy liquid comprises zinc sulfate,
    (3) said heavy liquid is injected into a bottom portion of said glass tube with a long needle syringe,
    (4) said centrifuging comprises
      (a) placing said glass tube in said centrifuge, and
      (b) spinning down said glass tube for about 15 minutes at about 2,000 RPM,
      (c) whereby waste sediment from said filtered fecal material is at said bottom portion, said zinc sulfate is directly above said waste sediment and below said live *E. bieneusi* organisms, and water is above said live *E. bieneusi* organisms,
    (5) said separation step comprises the steps of
      (a) removing essentially all the first-layer material in said first layer from said centrifugable material; and
      (b) filtering said first-layer material
      (c) wherein said filtering step comprises the steps of
        (i) a first filtering through an about-3-micron membrane pre-filter above a container with a vacuum source;
        (ii) a second filtering through about an *E.-bieneusi*-size screen of about 1 micron to remove most of said live *E. bieneusi* organisms;
        (iii) placing said removed live *E. bieneusi* organisms into a clean container with a small amount of purified water;

(iv) a third filtering through a less-than-*E.-bieneusi* size screen of about 0.4 micron to remove any remaining said live *E. bieneusi* organisms from said purified water, and (v) placing said remaining live *E. bieneusi* organisms into said clean container to provide purified live *E. bieneusi* organisms;

c. adding sufficient bacteria suppressant to said purified live *E. bieneusi* organisms to suppress any bacteria
  i. wherein about 50 mg. of gentamycin sulfate is added to each 1 cc. of said live *E. bieneusi* organisms;

d. sealing and refrigerating said clean container, for storage until use.

\* \* \* \* \*